United States Patent [19]
Madore

[11] Patent Number: 5,460,612
[45] Date of Patent: Oct. 24, 1995

[54] VASCULAR ACCESS PORT STABILIZING TOOL

[76] Inventor: Linda E. Madore, 49 Rosewood Dr., Saco, Me. 04072

[21] Appl. No.: 308,425

[22] Filed: Sep. 19, 1994

[51] Int. Cl.[6] ............................. A61M 5/48; A61M 5/42
[52] U.S. Cl. ............................. 604/116; 604/115
[58] Field of Search ....................... 604/115, 116, 604/157

[56] References Cited

U.S. PATENT DOCUMENTS

| | | | |
|---|---|---|---|
| 938,597 | 11/1909 | Lombardo | 604/157 |
| 1,320,536 | 11/1919 | Di Falco et al. | 604/157 |
| 1,561,116 | 11/1925 | Silliman | 604/115 |
| 1,991,103 | 2/1935 | King | 604/157 |
| 2,047,010 | 7/1936 | Dickinson | 604/157 |
| 2,234,961 | 3/1941 | Canada | 604/115 |
| 2,730,099 | 1/1956 | Sullivan | 604/157 |
| 4,314,568 | 2/1982 | Loving | 604/116 |
| 4,586,924 | 5/1986 | Lanning | 604/115 |
| 4,667,679 | 5/1987 | Sahota | 604/116 |
| 5,147,307 | 9/1992 | Gluck | 604/116 |

Primary Examiner—Paul J. Hirsch
Attorney, Agent, or Firm—Frederick R. Cantor

[57] ABSTRACT

A hand tool is provided for immobilizing an implanted vascular access port in the body of a patient while a hypodermic needle is being withdrawn from an elastomeric septum that forms a seal for the access port. The tool includes an elongated handle and a V-shaped prong structure designed to straddle the needle so that the prongs apply a restraining force on the implanted access port. The skin-contact surfaces of the prongs are convexly curved, such that the prongs apply the desired force, whatever the position of the handle. The tool can be held in a range of different positions while still applying the necessary restraining force.

7 Claims, 1 Drawing Sheet

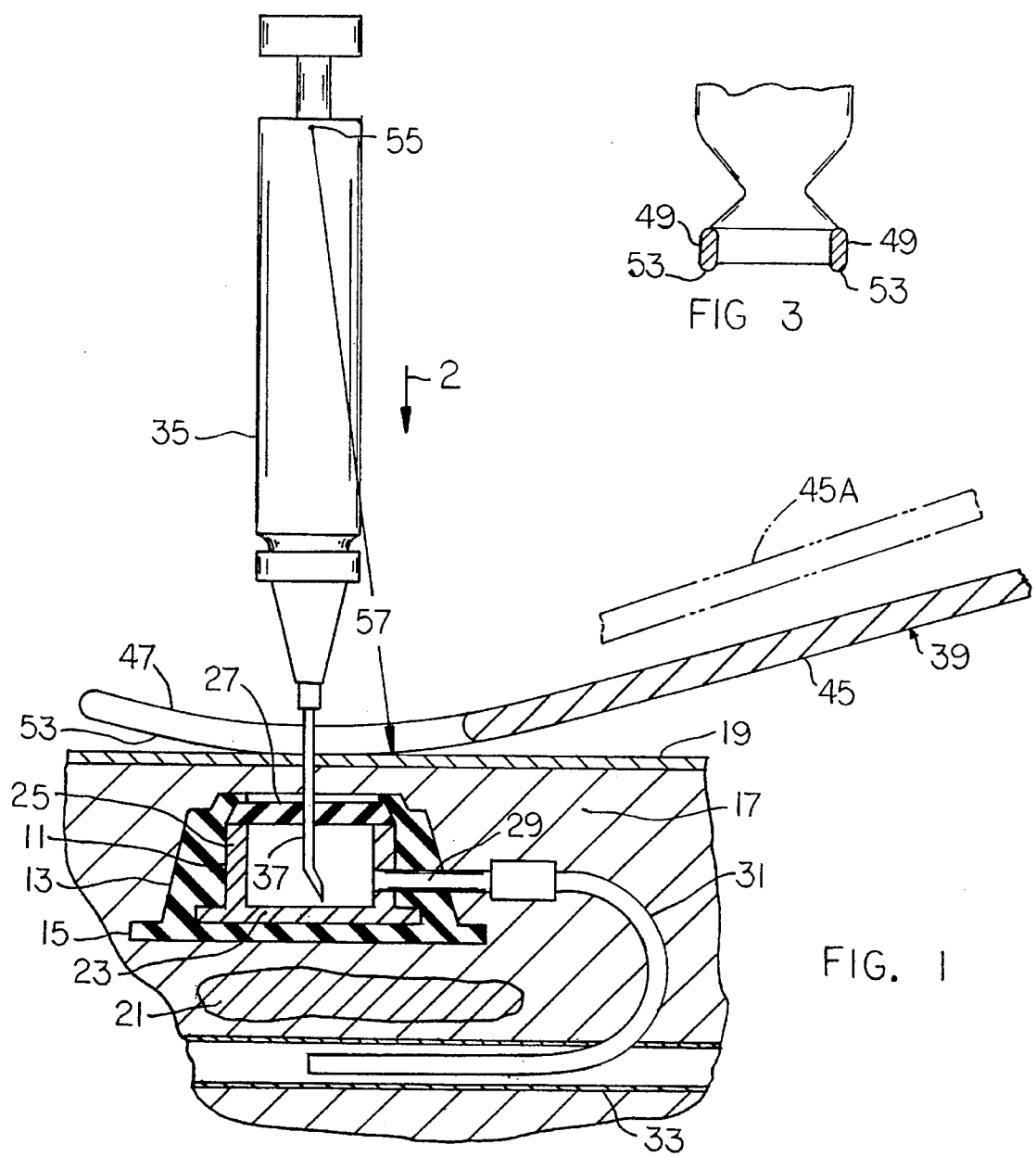
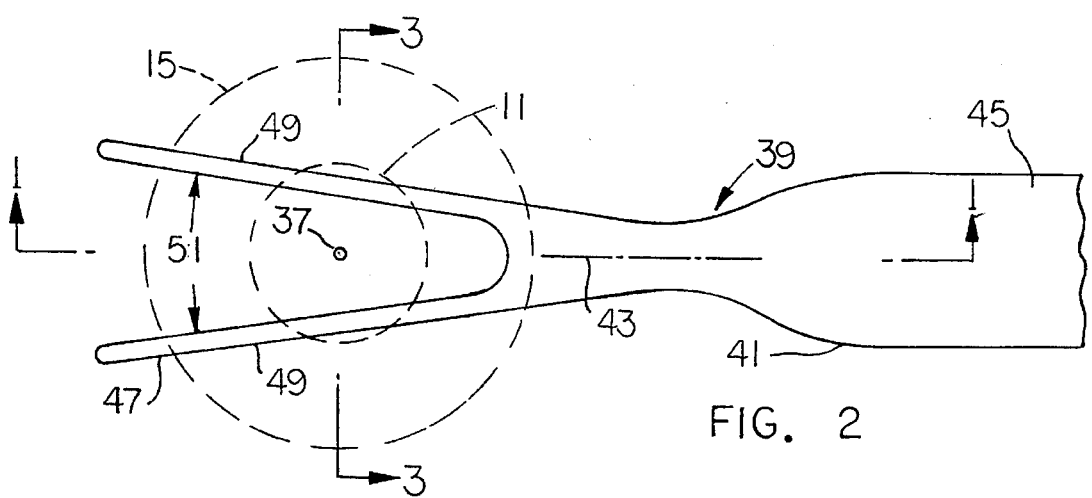

VASCULAR ACCESS PORT STABILIZING TOOL

BACKGROUND OF THE PRESENT INVENTION

1. Field of the Invention

The Present invention relates to devices used with vascular access ports.

The present invention relates to vascular access ports implanted under the skin of a patient, and, more particularly, to a tool for stabilizing the vascular access port while a hypodermic needle is being withdrawn from the port.

2. Prior Developments

A vascular access port comprises a reservoir surgically implanted in the subcutaneous tissue, below a patient's skin, to facilitate medical access to a blood vessel (e.g., a vein or artery). The reservoir has a fluid connection with a catheter tube leading to the blood vessel, whereby a fluid path is established between the reservoir and the blood vessel.

The implanted reservoir has a relatively thick elastomeric wall, or septum, facing the patient's skin, such that a hypodermic needle (or syringe needle) can be inserted through the skin and elastomeric wall, for withdrawing fluid from the reservoir, or injecting fluid into the reservoir.

The implanted vascular access port can be used to intermittently deliver liquid medications to the associated blood vessel, or to withdraw blood from the blood vessel. Such vascular access ports are usually employed in cases where the patient requires infusion therapy for an extended period of time, e.g., six months or more. They are surgically removed when no longer needed, or in the event that the patient finds them to be uncomfortable, or impractical, for daily self use.

One problem associated with implanted vascular access ports is that the elastomeric septum on the reservoir needs to be relatively thick, in order to seal against the needle side surface, and to close the needle opening when the needle is withdrawn from the vascular access port. During the process of withdrawing the needle out of the elastomeric septum, the septum material tends to grip the side surface of the needle so that the reservoir tends to be pulled along with the needle.

As a reaction to the needle sticking action, the nurse (or patient) exerts a greater pulling force on the hypodermic, such that the needle suddenly breaks away from the elastomeric septum. The sudden movement of the hypodermic needle can produce an involuntary movement of the hypodermic needle back toward the patient's or nurse's skin, and a possible penetration of the needle back into the skin surface. Such penetration can be dangerous (infections), as well as, painful and annoying.

The pulling action on the reservoir is somewhat disconcerting to the patient, in that the patient may feel that the reservoir is becoming detached from the subcutaneous tissue, thus requiring corrective surgery to restitch the reservoir to the tissue. Any shifting, or movement, of the implanted reservoir, is undesirable.

SUMMARY OF THE PRESENT INVENTION

An object of the present invention is to provide a device used in conjunction with vascular access ports.

Another object of the present invention is to provide a hand-operated tools that can be used to stabilize the reservoir of an implanted vascular access port while a hypodermic needle is being withdrawn from the access port. The tool keeps the vascular access port from shifting, while allowing the nurse or patient to exert a steady withdrawing force on the hypodermic needle. The needle-withdrawal process tends to be smoother and continuous, with less effort and with a lessened possibility for the needle to rebound back into the skin.

In one particular embodiment of the invention, the tool comprises an elongated handle and two prongs extending from the handle in a V configuration. The prongs have convexly curved skin-contact surfaces arranged to seat firmly against the patient's skin in a location overlying the implanted vascular access port.

The patient, or nurse, can hold the tool in one hand so that the prongs press against the skin surface. At the same time the hypodermic needle is withdrawn from the elastomeric septum on the vascular access port reservoir. The manual pressure on the prongs is transmitted through the patient's skin and subcutaneous tissue so that the reservoir is stabilized, i.e., held in a stationary position. The needle can then be withdrawn in a smooth continuous motion, thus minimizing the possibility for needle rebound shock or needle rebound skin penetration. Pain, and danger of infection, associated with the needle withdrawing process is thereby reduced.

The tool of the present invention functions as an extension of the nurse's fingers, so that the nurse is not required to apply finger pressure directly on the skin area immediately proximate to the needle penetration point. This reduces the risk of dangerous infection to the nurse or to the patient. There is no danger that a needle containing potentially infectious blood, or fluids, can be injected into the nurse's fingers, or the patient's skin.

In summary, and in accordance with the above discussion, the foregoing objectives are achieved in the following embodiments.

1. A tool facilitating the removal of a hypodermic needle from a vascular access port located in the subcutaneous tissue of a patient, comprising:

an elongated tool body having a longitudinal mid plane;

said tool body including a handle and a V-shaped prong means extending longitudinally from said handle;

said prong means and handle being symmetrical around said mid plane;

said V-shaped prong means comprising two prongs divergent in a transverse plane normal to said mid plane, whereby said prongs can be positioned on the patient's skin in a location overlying the vascular access port while a hypodermic needle is extended into said port;

said prongs being curved in planes paralleling the tool body mid plane, so that each prong has a convexly curved skin-contact surface; and the radius of curvature of each prong skin contact surface being substantially greater than the prong length, whereby the prongs can be engaged with the person's skin at any point along the prong length without reducing the prong area in contact with the person's skin.

2. The tool, as described in paragraph 1, wherein the radius of curvature of each prong skin-contact surface is approximately four inches.

3. The tool, as described in paragraph 2, wherein each prong has a length of about two inches.

4. The tool, as described in paragraph 1, wherein the radius of curvature of each prong skin-contact surface is approximately twice the prong length.

5. The tool, as described in paragraph 1, wherein said prongs diverge at an angle of about seventeen (17) degrees.

6. The tool, as described in paragraph 1, wherein each prong is linear, viewed in a direction parallel to the tool body mid plane; and each prong having a constant cross section along the prong length.

7. The tool, as described in paragraph 6, wherein the skin-contact surface on each prong has a semi-circular profile.

BRIEF DESCRIPTION OF THE DRAWINGS OF THE PRESENT INVENTION

FIG. 1, is a sectional view taken through a tool of the present invention, along line 1—1 in FIG. 2. The tool is shown in the position that it takes on the patient's skin during the process of withdrawing a hypodermic needle from an implanted vascular access port.

FIG. 2, is a top plan view of the tool shown in FIG. 1. FIG. 2, is taken in the direction of arrow 2 in FIG. 1.

FIG. 3, is a fragmentary sectional view taken on line 3—3 in FIG. 2.

DESCRIPTION OF THE PREFERRED EMBODIMENTS OF THE PRESENT INVENTION

FIG. 1, is a sectional view taken through a tool of the present invention, along line 1—1 in FIG. 2. The tool is shown in the position that it takes on the patient's skin during the process of withdrawing a hypodermic needle from an implanted vascular access port.

FIG. 1, illustrates a conventional access port implanted underneath the skin of a human patient. As shown, the vascular access port comprises a reservoir 11 encapsulated within an elastomeric sheath 13. The sheath 13 has a flange 15 that is stitched to a muscle in the subcutaneous tissue 17 underlying the patient's skin 19. A pocket is surgically formed in tissue 17 to accommodate the sheathed reservoir 11. The sheathed reservoir 11 is sometimes referred to as a portal. Often the sheathed reservoir is placed over a bone, e.g. bone 21, to help stabilize the reservoir 11 in the patient's body.

Reservoir 11 is a rigid structure that includes a bottom wall 23 and an upstanding annular side wall 25. The mouth of the reservoir 11 is covered (closed) by an elastomeric disk (or septum) 27. Reservoir 11 can be formed of various materials, e.g. titanium, stainless steel, or molded rigid plastic. Septum 27 may be constructed of silicone rubber, or other suitable material, of sufficient thickness to be self-sealing when subjected to repeated puncturing by a hypodermic needle.

Reservoir 11 has a tubular duct 29 extending through elastomeric sheath 13 to connect with a flexible catheter tube 31. The terminal end of tube 31 extends into a blood vessel 33 to establish a fluid path between reservoir 11 and the blood vessel 33. The blood vessel 33 can be a vein or artery. The catheter is implanted into the patient's body as an initial step in the surgical procedure for implanting the sheathed reservoir 11.

Blood materials, medications, and intravenous fluids can be introduced into the patient's body by injecting fluid from a hypodermic (syringe) 35 into reservoir 11. The catheter tube 31 transfers the injected fluid into the associated blood vessel 33. Blood samples can also be taken by inserting the hypodermic into reservoir 11. In either case, it is necessary to insert the hollow hypodermic needle 37 through the elastomeric septum 27 to establish a fluid connection between reservoir 11 and the hypodermic. After the infusion (or fluid extraction) is accomplished, the hypodermic needle 37 is withdrawn out of septum 27. The septum material is self-sealing when the needle leaves the septum 27, such that the septum can withstand multiple punctures without leaking.

It was previously noted that there is a problem in that while the hypodermic needle 37 is being moved out of the reservoir 11 the elastomeric septum 27 material tends to grip the needle side surface, such that the sheathed reservoir tends to be pulled upwardly (outwardly) along with the needle 37. The present invention is concerned with a tool 39 for stabilizing (or immobilizing) reservoir 11, while the hypodermic needle 37 is passing upwardly through septum 27.

FIG. 2, is a top plan view of the tool shown in FIG. 1. FIG. 2, is taken in the direction of arrow 2 in FIG. 1.

FIG. 3, is a fragmentary sectional view taken on line 3—3 in FIG. 2.

Tool 39 comprises an elongated tool body 41 having an imaginary longitudinal mid plane 43 (FIG. 2). In FIG. 1, mid plane 43 coincides with the plane of the paper. The tool 41 body includes a flat blade-like handle 45, and a V-shaped prong means 47 extending longitudinally from the handle 45. The handle 45 and prong means 47 are symmetrical around mid plane 43.

As shown in FIG. 2, the V-shaped prong means 47 comprises two prongs 49 diverging from each other in a transverse plane normal to mid plane 43. The preferred angle of divergence 51 of the prongs is approximately seventeen (17) degrees.

As viewed in FIG. 2, prongs 49 are linear in nature, i.e. the side surfaces of each prong are straight and essentially parallel. Each prong 49 has a transverse cross section that is generally constant along the length of the prong.

FIG. 3, illustrates a preferred prong cross-sectional configuration. The lower surface 53 of each prong, has a semi-circular profile, such that when the prongs are firmly pressed against the patient's skin 19, the surface of each prong will be imbedded in the skin without cutting or scratching the skin surface. The semi-circular surfaces 53 are devoid of sharp edges that might exert a cutting action on the patient's skin.

As viewed in side elevation (FIG. 1), the skin-contact surface 53 of each prong 49 is convexly curved around an imaginary center 55 located an appreciable distance above the prong plane. The radius of curvature 57 of each prong skin-contact surface 53 is preferably about twice the prong length, such that prong surfaces 53 have extensive contact with the patient's skin 19.

Prior to the process of withdrawing the hypodermic needle 37 out of elastomeric septum 27, tool 39 is positioned so that prongs 49 are aligned with reservoir 11 on either side of needle 37. As shown in FIG. 2, prongs 27 straddle the needle in overlying relation to the implanted reservoir 11.

The nurse, or patient, grips the tool handle 45 with one hand, while withdrawing the hypodermic needle 37 with the other hand. Pressure exerted by prongs 49 on the patient's skin is transmitted through the subcutaneous tissue 17 to the sheathed reservoir 11. The reservoir 11 is thus restrained, or immobilized, against upward movement with the hypodermic needle 37. The needle can therefor be withdrawn from septum 27 smoothly and quickly, with minimal disturbance to the sheathed reservoir 11 or its connection with catheter tube 31.

Due to the convex curvature of the prong surfaces 53 (as seen in FIG. 1), the tool 39 has effective contact with the patient's skin 19, even though handle 45 might be held at an angle different than that shown in FIG. 1. For example, if the handle 45 were tilted toward a more abrupt position, as shown by dashed line 45A, the prong surfaces 53 would still have effective engagement with the patient's skin. It is not necessary that the handle 45 be held at the precise angle shown in full lines in FIG. 1. The radius of curvature 57 designed into the skin-contact surfaces 53 enables the tool 39 to have a rocking motion on the patient's skin, so that the tool 39 can be held at a comfortable angle while still applying the necessary restraining force on the implanted vascular access port, i.e., reservoir 11.

The V-shaped configuration of the prongs 49 (as viewed in FIG. 2) is for the purpose of easy insertion of the tool 39 past (across) the hypodermic needle 37, while avoiding contact between the prongs 49 and the needle 37. Such contact could possibly be painful to the patient and also produce leakage at the joint between the needle 37 and septum 27.

As shown in FIG. 2, needle 37 is located midway between the two prongs 49. However, in practice such a precise positionment of the tool 39 relative to the needle may not always be accomplished. The needle can be relatively close to one prong, and relatively far away from the other prong while still having an operative arrangement. The principal requirement is that the prongs be reasonably centered around the needle so that the prongs are aligned with reservoir 11 for applying the necessary restraining force.

The tool can be constructed in various sizes and configurations. Typically each prong 49 will have a length of about two inches; the radius of curvature 57 will be about four inches. The overall length of the tool can be about eight inches. The tool is preferably made out of a single piece of stainless steel or other material, that can thermally withstand heat and chemical sterilization processes.

The drawings show a vascular access port having an elastomeric septum 27 as the roof for the reservoir 11. This type of vascular access port is sometimes referred to as a top entry port. There is another type of vascular access port, termed a side entry port. In the side entry port construction the reservoir has a frustum shape; the elastomeric septum constitutes one of the slanted side walls of the reservoir 11. The hypodermic needle 37 is inserted at an angle to the skin surface to penetrate the septum.

The tool of the present invention is usable with either the top entry device or the side entry device. In either case, the tool is used to apply a restraining force on the implanted reservoir, whereby the needle withdrawing operation can be carried out smoothly, and with minimum pain or discomfort to the patient. The tool action helps to prevent needle rebound and needle penetration, or stick, associated with such rebound. The tool acts as an extension of the nurse's fingers, such that the nurse does not have to place the fingers proximate to the needle while applying a restraining force on the implanted vascular access port. The restraining force is applied by the tool, not the nurse's fingers.

The present invention provides a vascular access port stabilizing tool. The drawings herein necessarily depict specific structural features and embodiments of the vascular access port stabilizing tool.

However, it will be appreciated by those skilled in the arts pertaining thereto, that the present invention can be practiced in various alternate forms and configurations. Further, the previously detailed descriptions of the preferred embodiments of the present invention, are presented for purposes of clarity of understanding only, and no unnecessary limitations should be implied therefrom. Finally, all appropriate mechanical and functional equivalents to the above, which may be obvious to those skilled in the arts pertaining thereto, are considered to be encompassed within the claims of the present invention.

What is claimed is:

1. A tool facilitating the removal of a hypodermic needle from a vascular access port located in the subcutaneous tissue of a patient, comprising:

an elongated tool body having a longitudinal mid plane;

said tool body including a handle and a V-shaped prong means extending longitudinally from said handle;

said prong means and handle being symmetrical around said mid plane;

said V-shaped prong means comprising two prongs divergent in a transverse plane normal to said mid plane, whereby said prongs can be positioned on the patient's skin in a location overlying the vascular access port while a hypodermic needle is extended into said port;

said prongs being curved in planes paralleling the tool body mid plane, so that each prong has a convexly curved skin-contact surface; and the radius of curvature of each prong skin contact surface being substantially greater than the prong length, whereby the prongs can be engaged with the person's skin at any point along the prong length without reducing the prong area in contact with the person's skin.

2. The tool, as described in claim 1, wherein the radius of curvature of each prong skin-contact surface is approximately four inches.

3. The tool, as described in claim 2, wherein each prong has a length of about two inches.

4. The tool, as described in claim 1, wherein the radius of curvature of each prong skin-contact surface is approximately twice the prong length.

5. The tool, as described in claim 1, wherein said prongs diverge at an angle of about seventeen (17) degrees.

6. The tool, as described in claim 1, wherein each prong is linear, viewed in a direction parallel to the tool body mid plane; and each prong having a constant cross-section along the prong length.

7. The tool, as described in claim 6, wherein the skin-contact surface on each prong has a semi-circular profile.

\* \* \* \* \*